United States Patent [19]
Albal et al.

[11] Patent Number: 5,194,067
[45] Date of Patent: Mar. 16, 1993

[54] RECOVERY OF HYDROGEN PEROXIDE

[75] Inventors: Rajendra S. Albal; Robert N. Cochran; David W. Leyshon, all of West Chester; Lawrence M. Candela, Philadelphia, all of Pa.

[73] Assignee: Arco Chemical Technology, L.P., Wilmington, Del.

[21] Appl. No.: 905,979

[22] Filed: Jun. 29, 1992

[51] Int. Cl.⁵ .................. B01D 12/00; C01B 15/026; C07C 45/00
[52] U.S. Cl. .................. 23/293 R; 423/591; 423/658.5; 568/320
[58] Field of Search ............. 568/320; 423/591, 658.5; 23/293 R

[56] References Cited
U.S. PATENT DOCUMENTS

| | | | |
|---|---|---|---|
| 2,819,949 | 1/1958 | Keeler et al. | 23/207 |
| 2,869,989 | 1/1959 | Keeler et al. | 23/207 |
| 2,871,102 | 1/1959 | Rust et al. | 23/207 |
| 2,871,103 | 1/1959 | Skinner et al. | 23/207 |
| 2,871,104 | 1/1959 | Rust | 23/207 |
| 2,949,343 | 8/1960 | Hood et al. | 23/207 |
| 3,003,853 | 10/1961 | Mecorney et al. | 23/207 |
| 3,012,860 | 12/1961 | Meeker et al. | 23/207 |
| 3,074,782 | 1/1963 | Meeker et al. | 23/207 |
| 3,351,635 | 11/1967 | Kollar | 260/348.5 |
| 4,303,632 | 12/1981 | Gosser | 423/591 |
| 4,897,085 | 1/1990 | Cochran et al. | 568/320 |
| 4,897,085 | 1/1990 | Cochran et al. | 23/293 |
| 4,897,252 | 1/1990 | Cochran et al. | 568/320 |
| 4,897,252 | 1/1990 | Cochran et al. | 423/591 |
| 4,994,625 | 2/1991 | Albal et al. | 423/591 |

Primary Examiner—Wayne Langel
Attorney, Agent, or Firm—William C. Long

[57] ABSTRACT

A process is provided whereby the hydrogen peroxide-containing oxidate from methyl benzyl alcohol oxidation is extracted with water and with ethyl benzene extractive solvent and an aqueous hydrogen peroxide phase is separated from an ethyl benzene solvent phase which also contains methyl benzyl alcohol and acetophenone, the improvement being that ethyl benzene is introduced into the extraction zone below the point of introduction of the oxidate, thus avoiding the possibility of formation of an aqueous hydrogen peroxide phase concentrated to a hazardous degree in hydrogen peroxide in the extraction zone.

2 Claims, 1 Drawing Sheet

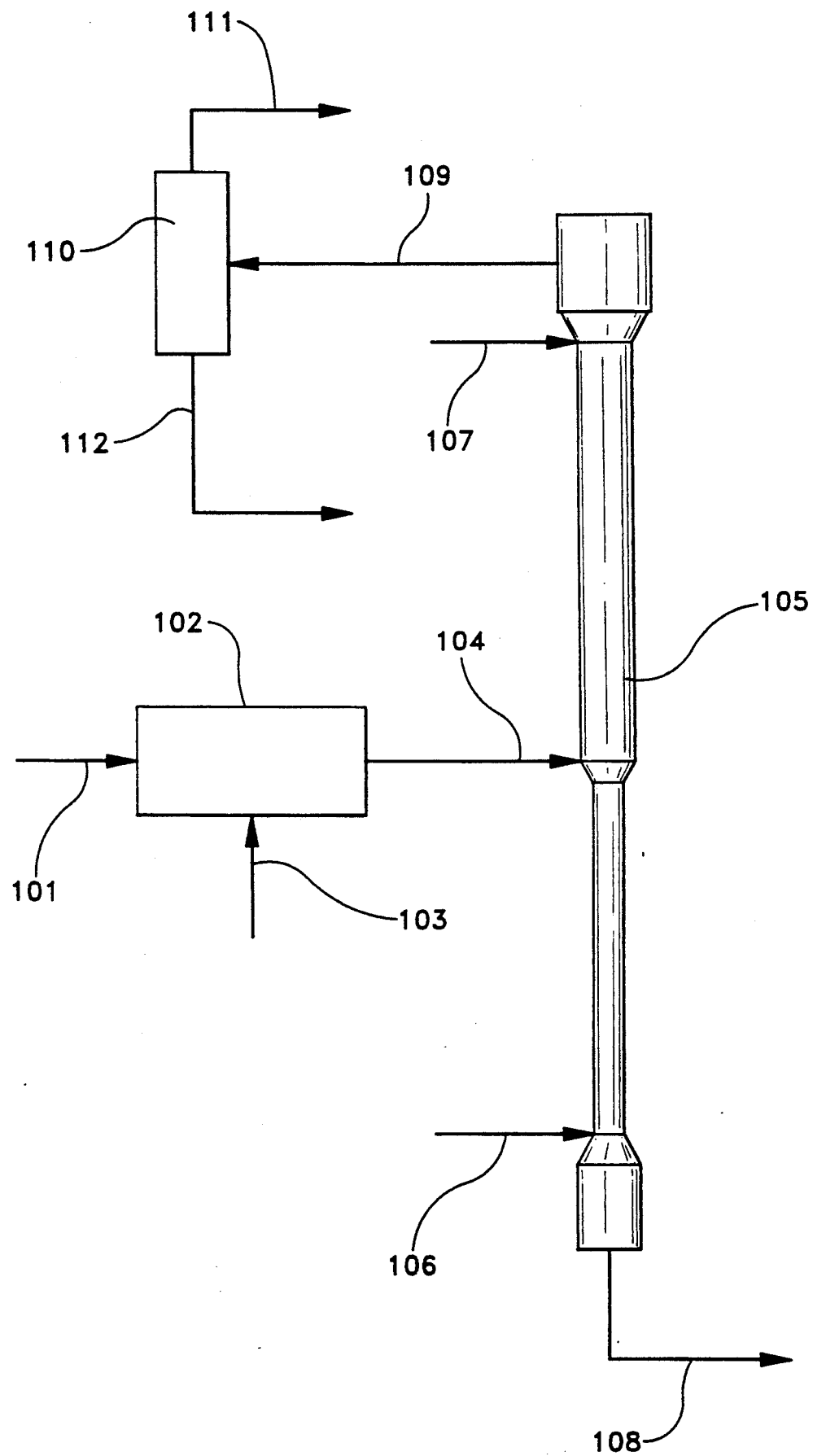

RECOVERY OF HYDROGEN PEROXIDE

BACKGROUND OF THE INVENTION

1. Field of the Invention

The present invention relates to the separation of hydrogen peroxide from methyl benzyl alcohol oxidate by water and ethyl benzene extraction.

2. Description of the Prior Art

Hydrogen peroxide is an important chemical of commerce which is produced in very large quantities for use in a number of industrial applications. The predominant process used commercially for the production of hydrogen peroxide involves the oxidation of anthrahydroquinone, extraction of hydrogen peroxide and reduction of the resulting anthraquinone to anthrahydroquinone which is reused. This process requires very high capital expenditures in that use of a working solvent with efficient recycle of various process components is a necessity.

Substantial efforts have been directed to processes which involve direct combination of hydrogen and oxygen but thus far such processes have not found widespread success.

Hydrogen peroxide has been formed by the oxidation of secondary alcohols. At one time the production of hydrogen peroxide by oxidation of isopropanol was practiced commercially. Other secondary alcohols which have been mentioned as starting materials for hydrogen peroxide production include 1-phenyl ethanol (methyl benzyl alcohol) and cyclohexanol. See, for example, U.S. Pat. Nos. 2,871,102–4 of Shell Development. In such prior procedures, difficulties have been encountered in the separation and recovery of product hydrogen peroxide from the secondary alcohol oxidate mixtures. See, for example, Shell U.S. Pat. Nos. 2,819,949, 2,869,989, 2,949,343, 3,003,853, 3,012,860 and 3,074,782.

Hydrogen peroxide has also been formed by oxidation of very high boiling secondary alcohols such as diaryl methanol, the product hydrogen peroxide being stripped from the reaction mixture during oxidation; see U.S. Pat. No. 4,303,632.

In certain commercial technologies, there are produced substantial quantities of various secondary alcohols. For example, in the coproduction of propylene oxide and styrene monomer by the reaction of ethyl benzene hydroperoxide with propylene, methyl benzyl alcohol is formed and ultimately converted by dehydration to styrene monomer. See U.S. Pat. No. 3,351,635.

In U.S. Pat. No. 4,897,085, a process is described for the production of hydrogen peroxide by oxidation of methyl benzyl alcohol containing streams, such as those formed in the Oxirane process.

In U.S. Pat. No. 4,897,252, a process for the recovery of hydrogen peroxide from methyl benzyl alcohol oxidation mixtures by ethyl benzene extraction is described. The present invention provides a further improvement in this process.

SUMMARY OF THE INVENTION

In the process of U.S. Pat. No. 4,897,085 there is provided an improved process for the recovery of hydrogen peroxide from methyl benzyl alcohol oxidate involving the use of ethyl benzene as an extractive solvent. Efficient separation is achieved, and the process is especially advantageous in that only materials normally found in the commercial propylene oxide/styrene monomer process are employed in the instant separation and recovery. In said process, ethyl benzene is admixed with the hydrogen peroxide containing oxidate, and the admixture is subjected to countercurrent extraction with water to separate hydrogen peroxide. The present invention represents the further improvement over said process wherein ethyl benzene is introduced into the water extraction column at a point below the oxidate point of introduction such that the water and the ethyl benzene contact the oxidate feed at essentially the same point. This procedure avoids problems which might occur where the oxidate and ethyl benzene are admixed prior to contact with the extraction water where there is a tendency for the formation of a potentially hazardous separate aqueous phase highly concentrated in hydrogen peroxide. In especially advantageous operation, the extraction is carried out in a single column with the organic phase as the continuous phase.

BRIEF DESCRIPTION OF THE DRAWING

The accompanying drawing illustrates in schematic form a suitable embodiment of the invention.

DETAILED DESCRIPTION OF THE INVENTION

In U.S. Pat. No. 4,897,252 there is described a method for the production of hydrogen peroxide by oxidation of methyl benzyl alcohol with molecular oxygen. Acetophenone is a coproduct of the oxidation.

The present invention provides an effective method for the recovery of hydrogen peroxide from methyl benzyl alcohol oxidate reaction mixtures such as those formed in the process described in said patent.

In accordance with the invention, the methyl benzyl alcohol oxidate mixture, which comprises methyl benzyl alcohol, acetophenone and hydrogen peroxide, is subjected to water extraction in an extraction column to separate product hydrogen peroxide. Ethyl benzene is also employed as an extractive solvent to enhance the separation of organic and inorganic materials. A key feature of the present inventive process is the provision for the addition of ethyl benzene to the extraction column at a point below the point of introduction of the oxidate mixture. Water is, of course, introduced at an upper point and flows downwardly as it extracts hydrogen peroxide. Ethyl benzene flows upwardly and serves to enhance separation of acetophenone and unreacted methyl benzyl alcohol from aqueous hydrogen peroxide. The lower section of the extraction column, rich in ethyl benzene, extracts organics from the aqueous phase containing hydrogen peroxide, while the upper section extracts hydrogen peroxide from the oxidate.

By introducing ethyl benzene below the oxidate point of introduction, the oxidate effectively contacts both the downflowing water extractant and the upflowing ethyl benzene extractant at the same time, and as a result the formation of a separate, aqueous phase highly concentrated in hydrogen peroxide is avoided. Ethyl benzene reduces the solubility of water and hydrogen peroxide in the oxidate. If ethyl benzene is added such that it is admixed with oxidate without sufficient water present, a concentrated hydrogen peroxide in water mixture (possibly over 70% hydrogen peroxide) tends to phase out.

It is preferred to carry out the extractive separation in a single extraction column since, with a plurality of columns, aqueous hydrogen peroxide must be pumped from one zone to another, thus introducing potential hazards into the operation. It is also preferred to use the organic as the continuous phase in the extraction zone.

The use of ethyl benzene as the extractive solvent for recovery of hydrogen peroxide from methyl benzyl alcohol oxidate has certain unique advantages as described in U.S. Pat. No. 4,897,085. In the first place, ethyl benzene is highly effective as the extractive solvent. Unreacted methyl benzyl alcohol as well as acetophenone are extracted into the ethyl benzene solvent while water and hydrogen peroxide are effectively excluded. In the second place, ethyl benzene is an essential feedstock in the commercial propylene oxide/styrene monomer process which also can provide the methyl benzyl alcohol for the hydrogen peroxide production. Thus there is outstanding synergy between the technologies.

Referring to FIG. 1, a methyl benzyl alcohol stream is introduced via line 101 into oxidation reactor 102. Most suitably, the methyl benzyl alcohol stream also comprises acetophenone and represents a process stream conventionally available from propylene oxide/styrene monomer technology. Methyl benzyl alcohol is oxidized in reactor 102 by contact with molecular oxygen introduced as air via line 103. Conditions of the oxidation to form hydrogen peroxide and acetophenone are as described in U.S. Pat. No. 4,897,085, the contents of which are incorporated herein by reference.

Liquid reaction mixture is withdrawn from reactor 102 via line 104 and this oxidate comprises unreacted methyl benzyl alcohol, acetophenone oxidation coproduct as well as such acetophenone as may be present with the methyl benzyl alcohol feed, and hydrogen peroxide product. Small amounts of water may also be present, below 4% by weight of the reaction mixture, preferably below 2% and most preferably below 1%. This oxidate mixture passes to the intermediate section of solvent extraction column 105.

An ethyl benzene stream is introduced via line 106 to extraction column 105 at a point below the point of introduction of the oxidate, preferably near the bottom as shown. The light organic phase passes upwardly in 105, countercurrently contacting a heavy aqueous phase passing downwardly from the top, water being introduced via line 107 near the top of column 105. The $H_2O_2$ contained in the organic feed oxidate is extracted into the aqueous stream which exits from the bottom of the column via line 108.

The organic phase, now with $H_2O_2$ product removed, exits column 105 from the top via line 109 and passes to distillation column 110 wherein it is distilled to separate ethyl benzene overhead via line 111 from the higher boiling methyl benzyl alcohol/acetophenone mixture which is removed via line 112. The ethyl benzene can be recycled to the extraction or used elsewhere. The methyl benzyl alcohol/acetophenone is especially advantageously dehydrated in accordance with known procedures to form styrene monomer from the methyl benzyl alcohol, followed ultimately by hydrogenation of the acetophenone to produce more methyl benzyl alcohol.

In the anthraquinone-based technology currently employed, the extractions involve the aqueous phase as the continuous phase which results in large inventories of concentrated hydrogen peroxide in the extraction column. The inventory of concentrated hydrogen peroxide in the extraction column is reduced in the preferred practice of the invention wherein the organic phase is the continuous phase.

The aqueous hydrogen peroxide phase removed from column 105 can be treated by conventional procedures to further concentrate and purify the hydrogen peroxide product. In especially preferred practice, this stream is treated, as described in copending Ser. No. 07/905,961 filed on even date herewith, with an adsorptive resin to further remove organic impurities.

Practice of the invention avoids the case where ethyl benzene contacts the oxidate before extraction water, and thus avoids the formation of a separate aqueous phase concentrated in hydrogen peroxide to a possible hazardous level.

The following example illustrates the invention. Unless otherwise indicated, parts are weights per hour and percentages are by weight.

EXAMPLE

A methyl benzyl alcohol oxidate in amount of 1000 parts comprised of 56.0% methyl benzyl alcohol, 37.9% acetophenone, 5.3% $H_2O_2$ and 0.8% $H_2O$ is removed from oxidizer 102 by means of line 104. This stream is introduced into a Karr extraction column 105 at an intermediate point wherein there are three theoretical extraction stages both above and below the point of introduction. About 500 parts of an ethyl benzene stream is introduced into column 105 at a point near the bottom.

To the top of 105 is introduced 150 parts of a pure water stream. The extraction column 105 operates at 20° C. and atmospheric pressure. The organic product from column 105 in amount of 1445 parts, comprised of 34.6% ethyl benzene, 38.8% methyl benzyl alcohol, 26.2% acetophenone and 0.4% $H_2O$, exits the top of column 105 via line 109 and is sent to ethyl benzene distillation unit 110. The aqueous product from column 105 in amount of 205 parts, comprised of 200 ppm methyl benzyl alcohol, 200 ppm acetophenone, 25.8% $H_2O_2$ and 74.2% $H_2O$, exits the bottom of column 105 via line 108. This stream can be concentrated and further purified by conventional methods, but preferably is treated in accordance with the process described in copending Ser. No. 07/906,961 filed of even date herewith.

In column 105 the organic phase is the continuous phase. The upper and lower sections of column 105 have different diameters to maintain the same flow velocities in the two sections.

The ethyl benzene distillation unit 110 which receives organic product from the $H_2O_2$ extractor 105 via line 109 separates ethyl benzene for recycle to the extraction or for usage elsewhere. The overhead stream from 110 in amount of 506 parts comprised of 98.8% ethyl benzene and 1.2% $H_2O$ exits via line 111; the water can later be decanted from this stream. The bottoms product from 110 in amount of 939 parts comprised of 59.6% methyl benzyl alcohol and 40.4% acetophenone exits via line 112 and can be converted to styrene monomer in accordance with conventional procedures.

In operation as above indicated, most of the organic impurities which could cause explosion hazards are removed prior to the time the extract stream concentrated in hydrogen peroxide reaches the column bottom. Also by the use of one column, intermediate pumping of hydrogen peroxide is avoided.

I claim:

1. In a process for the extraction in an extraction zone of hydrogen peroxide from a methyl benzyl alcohol oxidate mixture containing methyl benzyl alcohol, acetophenone and hydrogen peroxide wherein ethyl benzene and water are employed as extractive solvents, water being introduced in the upper section of the extraction zone, the improvement which comprises introducing ethyl benzene solvent into the extraction zone at a point below the point of introduction of the oxidate mixture.

2. The process of claim 1 wherein the organic phase is the continuous phase in the extraction zone.

* * * * *